United States Patent [19]

Gamache et al.

[11] Patent Number: 5,686,488

[45] Date of Patent: Nov. 11, 1997

[54] POLYETHOXYLATED CASTOR OIL PRODUCTS AS ANTI-INFLAMMATORY AGENTS

[75] Inventors: Daniel A. Gamache, Arlington; Gustav Graff, Cleburne; Jon C. Nixon, Mansfield, all of Tex.

[73] Assignee: Alcon Laboratories, Inc., Fort Worth, Tex.

[21] Appl. No.: 519,327

[22] Filed: Aug. 25, 1995

[51] Int. Cl.$^6$ .................................................. A61K 31/23
[52] U.S. Cl. ........................ 514/549; 514/552; 514/914
[58] Field of Search .......................... 514/25, 549, 552, 514/563, 557, 914; 424/574, 679, 680, 681, 601, 717

[56] References Cited

U.S. PATENT DOCUMENTS

| | | | |
|---|---|---|---|
| 4,550,022 | 10/1985 | Garabedian et al. | 424/127 |
| 4,829,088 | 5/1989 | Doulakas | 514/567 |
| 4,960,799 | 10/1990 | Nagy | 514/567 |
| 4,975,419 | 12/1990 | Newton et al. | 514/6 |

FOREIGN PATENT DOCUMENTS

| | | |
|---|---|---|
| 3048000 A1 | 12/1980 | Germany. |
| WO 94/12198 | 6/1994 | WIPO. |

OTHER PUBLICATIONS

Campbell, W., "Lipid–derived Autacoids: Eicosanoids and Platelet–Activating Factor", Goodman and Gilman's *The Pharmacological Basis of Therapeutics*, pp. 600–617, Pergman Press, NY (1990).

Nelson, P., "Cyclooxygenase Inhibitors", *CRC Handbook of Eicosanoids: Prostaglandins, and Related Lipids*, vol. II, Drugs Acting Via the Eicosanoids, pp. 59–133, CRC Press, Boca Raton, FL (1989).

Brems, J., et al., "Effect of Cyclosporine and Steroids on Canine Bile Flow", *Hepatolog*, 14(3): 523–527 (1991).

Sewell, G., et al., "The Formulation and Stability of A Unit–Dose Oral Vitamin $K_1$ Preparation", *Journal of Clinical Pharmaccy and Therapeutics*, 13(1): 73–76 (1988).

Woodburn, K., et al., "Biodistribution and PDT Efficacy of a Ketochlorin Photosensitizer as a Function of the Delivery Vehicle", *Journal of Photochemistry and Photobiology*, 60(2), 154–159 (1994).

Lodge, N., "Direct Vasoconstrictor Effects of Sandimmune (Cyclosporine A) are Mediated by Its Vehicle Cremophor EL: Inhibition by the Thromboxane $A_2$/Prostaglandin Endoperoxide Receptor Antagonist Ifetroban", *Journal of Pharmacology and Experimental Therapeutics*, 27(2): 730–734 (1994).

Lazarus, J.H., et al., "Polyoxyethylene Castor Oil Derivatives", *Handbook of Pharmaceutical Excipients*, 10th Edition, pp. 221–224, American Pharmaceutical Association, Washington, D.C. (1986).

Chervinsky, D., et al., "Cremophor–EL Enhances Taxol Efficacy in a Multi–Drug Resistant C1300 Neuroblastoma Cell Line", *Anticancer Research* 13(1): 93–96 (1993).

Chuang, L., et al., "Cremophor EL Inhibits 12–O–Tetradecanoylphorbol–13–acetate (TPA)–Induced Protein Phosphorylation in Human Myeloblastic Leukemia ML–1 Cells", *Anticancer Research* 11(4): 1517–1521 (1991).

Furey, et al., Renovascular Effects of Nonprescription Ibuprofen in Elderly Hypertensive Patients with Mild Renal Impairment, *Pharmacotherapy*, vol. 13, No. 2, pp. 143–148 (1993).

van Delft, Comparison of the Effects of Corticosteroids and Indomethacin on the Response of the Blood–Aqueous Barrier to Injury, *Current Eye Research*, vol. 6, No. 3, pp. 419–425 (1987).

Bhattacherjee, An Evaluation of Ocular Inflammation Following the Injection of Bacterial Endotoxin into the Rat Food Pad, *Investigative Ophthalmology and Visual Science*, vol. 24, pp. 196–202 (1983).

Dicorieto, Characterization of the Adhesion of the Human Monocytic Cell Line U937 to Cultured Endothelial Cells, *Journal of Clinical Investigation*, vol. 75, pp. 1153–1161 (1985).

Goodwin, J., Anti–Inflammatory Drugs, *Basic and Clinical Immunology*, Eighth Edition, Appleton and Lange, D. Sites (editor), Norwalk, CT, pp. 786–790 (1994).

*The United States Pharmacopeia*, 22nd Edition; The National Formulary, 17th Edition, pp. 1966–1967 (1990).

Attwood, D., et al., *Surfactant Systems Their chemistry, pharmacy and biology*, Chapman And Hall, London New York, pp. 323, 337, 444–447, 460–468, and 645–657 (1985).

BASF brochure, "Cremophor EL", pp. 1–7 (1983).

Ash, Michael and Irene, *Handbook of Industrial Surfacants*, Gower Publishing Company, England, pp. 716–725 (1993).

*Inactive Ingrediant Guide*, Division of Drug Information Resources, Food and Drug Administration, Center for Drug Evaluation and Research, p. 103 (Oct., 1993).

Primary Examiner—Phyllis G. Spivack
Attorney, Agent, or Firm—Michael C. Mayo

[57] ABSTRACT

Compositions and methods treating inflammation are disclosed wherein the compositions contain a pharmaceutically effective anti-inflammatory amount of a polyethoxylated castor oil.

24 Claims, No Drawings

POLYETHOXYLATED CASTOR OIL PRODUCTS AS ANTI-INFLAMMATORY AGENTS

BACKGROUND OF THE INVENTION

The present invention is directed to polyethoxylated castor oil (PEO-CO) product compositions and methods of use for the treatment of inflammatory disorders.

Tissue injury (including surgery) or excessive cellular stress can cause inflammation and may lead to tissue damage and disease. Intimation has been implicated in numerous pathologies including atherosclerosis, rheumatoid arthritis and uveitis. Other inflammatory disorders are the result of toxic insult, aging and trauma, including surgery. Numerous biochemical pathways are known to lead to inflammation. In general, the cyclooxygenase system produces prostaglandins, while the lipoxygenase system produces leukotrienes, "HETEs". and "HPETEs." Such agents have been associated with intimation. See generally, *Goodman and Oilman's The Pharmacological Basis of Therapeutics*, pages 600–617, Pergman Press, NY (1990). Other agents synthesized and secreted by cells in the injured tissue, such as the cytokines, also mediate inflammatory responses.

Cellular action also contributes to inflammatory disorders. Examples of cellular action include the migration of neutrophils and monocytic phagocytes to the inflammation site, as well as to macrophage maturation and the formation of atherosclerotic foam cells.

Therapies designed to inhibit the promotion of these types of biochemical and cellular responses are therefore of great interest.

Numerous chemical entities have been discovered and implemented in therapies to prevent or reduce the inflammatory responses caused by the biochemical and cellular events described above. Such molecules have included steroidal anti-inflammatory agents, such as dexamethasone and cortisone; and non-steroidal anti-inflammatory agents (NSAIA), such as aspirin, indomethacin and ibuprofen. NSAIAs have been used extensively for the treatment of inflammatory disorders. These agents encompass a number of different chemical entities including indoles, arylacetic acids, and imidazoles. See generally, *CRC Handbook of Eicosanoids: Prostaglandins, and Related Lipids, Volume II, Drugs Acting Via the Eicosanoids*, pages 59–133, CRC Press, Boca Raton, Fla. (1989), for further background concerning this use of NSAIAs.

While each of these chemical therapies have advantages, they also possess disadvantages. For example, aspirin has been associated with stomach irritation. Moreover, ibuprofen has been found to have some negative renal effects especially on elderly patients with high blood pressure or those with already compromised renal function (S. A. Furey et al., Renovascular Effects of Nonprescription Ibuprofen in Elderly Hypertensive Patients with Mild Renal Impairment, *Pharmacotherapy*, volume 13, No. 2, pages 143–148 (1993)). Steroids, such as dexamethasone, can cause systemic side effects including hypertrophy of the liver, glycogen deposition in the liver, gluconeogenesis, renal effects, alterations in calcium and bone metabolism and ocular hypertension particularly when dosed topically to the eye (D. Sites et al., *Basic and Clinical Immunology*, Eighth Edition, Appleton and Lange, Norwalk, Conn. (1994), pages 786–790).

Polyethoxylated castor oils (PEO-CO) have been, and are continued to be used in the pharmaceutical industry as vehicles for drag delivery. PEO-COs are prepared by the ethoxylation of castor oil. Various PEO-COs used in the industry include polyoxyl 35 castor oil and polyoxyl 40 castor oil (*Inactive Ingredients Guide*, Division of Drug Information Resources, Food and Drug Administration, Center for Drug Evaluation and Research, page 103 (October, 1993)).

PEO-35 castor oil (PEO-35-CO), a PEO-CO, is a mixture of hydrophilic and hydrophobic molecules prepared by the ethoxylation of castor oil. PEO-35-CO has been used in the pharmaceutical industry in a myriad of applications. For example, PEO-35-CO has been used as a vehicle for cyclosporin A (*Hepatology*, volume 14, No. 3, pages 523–527 (1991)); as an intravenous vehicle for taxol (WIPO Publication No. WO 9412198 A1 (Elliott, et al.)); as a solubilizing agent for oral administration of Vitamin K (*Journal Clinical Pharmaceutical Therapy*, volume 13, No. 1, pages 73–76 (1988)); as a stabilizing agent for intramuscular administration of the $\beta$-carotene (German Patent No. DE 3048000 A1 (Hoppe, et al.)); and incorporated in liposomes containing cyclodextrin for the delivery of photosensitizing agents used in the photodynamic treatment of cancer (*Journal of Photochemistry and Photobiology*, volume 60, No. 2, pages 154–159 (1993)). Indeed, PEO-35-CO is listed in the *United States Pharmacopea* as a safe, recognized excipient for pharmaceutical applications.

PEO-35-CO has also been used in anti-inflammatory compositions for the treatment of the eye. U.S. Pat. Nos. 4,829,088 (Doulakas) and U.S. Pat. No. 4,960,799 (Nagy) disclose compositions containing an active non-steroidal anti-inflammatory agent and various excipients including PEO-35-CO. However, these patents disclose the use PEO-35-CO only as a solubilizing agent and do not propose the use of PEO-35-CO separately for anti-inflammatory therapy, or suggest the utility of PEO-35-CO as an active anti-inflammatory agent.

PEO-35-CO has also been shown to exhibit some effects of its own on various biochemical systems. For example, PEO-35-CO has been reported to mediate vasoconstrictor effects of cyclosporin A (*Journal of Pharmaceuticals and Experimental Therapeutics*, volume 271, No. 2, pages 730–734 (1994)), reverse the cross-resistance of taxol in a neuroblastoma cell line (*Anticancer Research* volume 13, No. 1, pages 93–96 (1993)), and inhibit protein kinase C activity in vitro (*Anticancer Research* volume 11, No. 4, pages 1517–1521 (1991)).

Though PEO-35-CO has been used extensively as an inactive excipient, it has never been proposed or used as an active additive or for exclusive use in the prevention, reduction or amelioration of inflammation.

SUMMARY OF THE INVENTION

The present invention is directed to compositions and methods of using polyethoxylated castor oil products for the prevention, reduction or amelioration (hereinafter "treatment") of inflammation. The present invention is particularly useful because the PEO-COs are known to be safe and free of the side effects associated with conventional agents used to treat inflammation. The present invention takes advantage of the surprising efficacy of PEO-COs with the known safety of these products to provide safe and effective compositions and methods for treating inflammation.

The present invention provides compositions of PEO-COs for pharmaceutical administration. Preferred compositions comprise an effective amount of at least one PEO-CO in topical ophthalmic or intraocular vehicles. The most preferred composition comprises PEO-35-CO in a physiologically balanced irrigating solution.

The methods of the present invention are directed to the administration of an effective amount of at least one PEO-CO to treat inflammation. Preferred methods are directed to the anterior and posterior intraocular administration of a surgical irrigating or vitreal replacement solution containing an effective amount of PEO-35-CO, during vitreoretinal or cataract extraction surgery.

DETAILED DESCRIPTION OF THE INVENTION

Compositions of the present invention contain an effective amount of at least one polyethoxylated castor oil or a polyethoxylated castor oil derivative, hereinafter referred collectively to as "PEO-CO," in an appropriate vehicle. Polyethoxylated castor oil derivatives are formed by the ethoxylation of castor oil with ethylene oxide. Castor oil is generally composed of about 87% ricinoleic acid, 7% oleic acid, 3% linoleic acid, 2% palmitic acid and 1% stearic acid. The reaction of varying molar ratios of ethylene oxide with castor oil yields different chemical products of PEO-COs. For example the use of a molar ratio of 5 yields a product known as PEO-5-CO.

The PEO-COs, suitable for use in the present invention, include products obtained from reacting from 2 to 200 moles of ethylene oxide per one mole of castor oil (*Handbook of Pharmaceutical Excipients*, 10th Edition, pages 221–224 American Pharmaceutical Association, Washington, D.C. (1986)). The compositions of the present invention can also be hydrogenated, yielding analogous hydrogenated PEO-COs. The most preferred PEO-CO is PE6-35-CO, also known as Cremophor EL®, (available from BASF Corporation, Parsippany N.J., USA). Other suitable PEO-COs include hydrogenated PEO-40-CO, also known as Cremophor RH 40®, and hydrogenated PEO-60-CO, also known as Cremophor RH 60® (both also available from BASF).

PEO-35-CO is a mixture of various hydrophobic and hydrophilic components. The hydrophobic components are predominantly (83%) esters of ricinoleic acid with glycerol/polyglycol ethers and some unaltered castor oil. The hydrophilic components (17%) consist of glycerol/polyglycol ethers and polyglycols. PEO-35-CO is produced by reacting one mole of castor oil with 35 to 40 moles of ethylene oxide. PEO-35-CO is a pale yellow, oily liquid used as a solubilizing agent or for wetting or emulsifying lipophilic/hydrophobic compounds. PEO-35-CO is commercially available from BASF and MAZER corporations in the United States, and from BASF, Blagden Campbell or GAF in the United Kingdom.

The compositions and methods of the present invention will employ an effective amount of one or more PEO-COs to treat inflammation. As used herein, "an effective amount" of a PEO-CO is that amount which prevents, reduces or ameliorates inflammation.

The products of the present invention may be contained in various types of pharmaceutical compositions, in accordance with formulation techniques known to those skilled in the art. For example, the products may be included in tablets, capsules, solutions, suspensions and other dosage forms adapted for oral administration; and solutions and suspensions adapted for topical, parenteral, intracameral or intravitreal use.

One preferred embodiment of the present invention is directed to the provision of compositions adapted for topical treatment of ophthalmic tissues for ocular inflammation. The ophthalmic compositions of the present invention will include at least one PEO-CO and a pharmaceutically acceptable vehicle. Various types of vehicles may be used for topical ophthalmic administration. The vehicles will generally be aqueous in nature. However, the PEO-COs of the present invention may also be readily incorporated into other types of compositions, such as suspensions, and viscous or semi-viscous gels. Suspensions may be preferred for PEO-COs which are less soluble in water. The ophthalmic compositions of the present invention may also include various other ingredients, such as buffers, preservatives, co-solvents and viscosity building agents.

An appropriate buffer system (e.g., bicarbonate, sodium phosphate, sodium acetate or sodium borate) may be added to prevent pH drift under storage conditions.

Ophthalmic products are typically packaged in multidose form. Preservatives are thus required to prevent microbial contamination after the package is opened. Suitable preservatives include: benzalkonium chloride, thimerosal, chlorobutanol, methyl paraben, propyl paraben, phenylethyl alcohol, edetate disodium, sorbic acid, chlorhexidine, polyquaternium-1, or other agents known to those skilled in the art. Such preservatives are typically employed at a level generally from 0.0001 to 1.0 % w/v.

Viscosity greater than that of simple aqueous solutions may be desirable to increase ocular absorption of the PEO-COs, to decrease variability in dispensing the formulations, to decrease physical separation of components of a suspension or emulsion and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 % w/v.

The route of administration (e.g., topical, parenteral, oral or intraocular) and the dosage regimen will be determined by skilled clinicians, based on factors such as the exact nature of the condition being treated, the severity of the condition, the age and general physical condition of the patient.

As indicated above, PEO-COs are used to prevent or reduce inflammation at humoral and cellular levels. PEO-COs may also be used as an adjunct to ophthalmic surgery, such as by intracameral, intravitreal or subconjunctival injection following ophthalmic surgery. PEO-COs may be used for acute treatment of temporary conditions, or may be administered chronically, especially in the case of degenerative disease. PEO-COs may also be used in bioreplacement fluids, for example, during vitrectomy surgery. PEO-COs may also be used prophylactically, especially prior to ocular surgery, noninvasive ophthalmic procedures, or other types of surgery.

Physiologically balanced irrigating solutions containing PEO-COs, for intraocular administration, are preferred compositions of the present invention. As used herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; an antioxidant/free radical scavenger, such as vitamin E, beta carotene, ascorbic acid, glutathione, cysteine or organic synthetics; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (available from Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference. Other irrigating solutions include BSS® Plus Sterile Irrigating Solution without the antioxidant, glutathione, present Another preferred embodiment of the present invention is directed to the use of PEO-COs in bioreplacement compositions. Preferred compositions will be formulated for use in vitreal surgery. Such compositions will mimic the vitreous, and will typically contain an effective amount of at least one PEO-CO; one or more glycosaminoglycans; physiologic ions, such as $Na^+$, $Cl^-$, $K^+$, $Ca^{++}$, and $Mg^{++}$; and water. Glyco saminoglycans (GAGs) useful in the viscous compositions of the present invention include chondroitin sulfate (COS), hyaluronic acid (HA), and keratin sulfate. These GAGs have average molecular weights between about 25,000 and about 2,000,000.

The dosage of PEO-COs used for any of the above-described purposes of topical, intraocular or systemic administration will vary due to the differences in patient sensitivities, severity of the condition being treated and the route of administration. In general, a range of from about 0.01 to 10 mg/kg of at least one PEO-CO will be administered to a patient orally or intravenously; 30 to 50 µL of a 0.01 to 10% w/v PEO-CO solution will be administered topically; and about 2–4 ml/minute (total volume will range, typically from 50–100 mL) of an irrigating solution containing 0.01 to 0.5% w/v of at least one PEO-CO will be administered intraocularly. As stated above, the actual dosage of PEO-COs will be determined by skilled clinicians, and will depend generally on the length of administration necessary, the severity of the condition and so on.

As used herein, the term "pharmaceutically acceptable carrier" refers to any formulation which is acceptable, i.e., safe and provides the appropriate delivery for the desired route of administration, of an effective amount of at least one PEO-CO of the present invention. As such, all of the above-described formulations of the present invention, and all of following formulation examples of the present invention are hereby referred to as "pharmaceutically acceptable carriers."

The present invention may be embodied in various types of formulations. Representative formulations are described in Examples 1–8 below:

EXAMPLE 1

The following two-part formulation is similar to the BSS Plus® Intraocular Irrigating Solution available from Alcon Laboratories, Inc., Fort Worth, Tex., USA. That product, which is described in U.S. Pat. No. 4,550,022 (Garabedian, et al.), consists of two solutions referred to as "Part I" and "Part II," respectively. The following description illustrates how that product or similar products could be modified to incorporate the present invention.

Part I is made by dissolving sodium chloride, potassium chloride, and anhydrous dibasic sodium phosphate in water for injection at about 20° C. Then sodium bicarbonate is added and dissolved. Additional water for injection is added to make the desired volume and 1N HCl is added to adjust the pH to about 7.4. The solution is then passed through a 0.45 micron Millipore filter and placed in a bottle. The filled bottle is then stoppered, evacuated and sealed. The sealed bottle is sterilized by autoclaving at 121° C for about 23 minutes.

Part II is made by dissolving calcium chloride dihydrate, magnesium chloride hexahydrate, dextrose, and optionally, oxidized glutathione in water for injection. The solution is then sterile filtered through a 0.22 micron membrane filter and aseptically filled into a presterilized bottle and sealed with a presterilized rubber stopper.

One or more PEO-COs for treating inflammation may be added in a range of from 0.01 to 0.5% w/v to either Part I or Part II, depending on the pKa of the PEO-CO selected.

When Parts I and II are combined, the composition of the resulting formulation is as follows:

| Ingredients | Concentration millimolar (mM) |
| --- | --- |
| Oxidized Glutathione | 0.01–10.0 |
| PEO-CO | 0.01 –0.5% (weight/volume) |
| Bicarbonate | 1–50 |
| Calcium | 0.1–5 |
| Magnesium | 0.1–10 |
| Potassium | 1–10 |
| Sodium | 50–500 |
| Phosphate | 0.1–5 |
| Glucose | 1–25 |
| Chloride | 50–500 |
| Sodium Hydroxide and/or Hydrochloric Acid | Adjust pH |
| Water for Injection | q.s. |

The invention may also be embodied in products formulated or configured differently from the two-part product described above. For example, the acidic solution containing oxidized glutathione can be lyophilized (i.e., freeze-dried) following preparation and then reconstituted as a solution prior to use. That type of formulation is described in U.S. Pat. No. 4,975,419.

EXAMPLE 2

Topical ophthalmic compositions useful for treating inflammation:

| Component | % w/v |
| --- | --- |
| PEO-CO | 0.05–10.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 3

A preferred topical ophthalmic compositions useful for treating inflammation:

| Component | % w/v |
| --- | --- |
| PEO-35-CO | 5.0 |
| Tyloxapol | 0.01–0.05 |
| HPMC | 0.5 |
| Benzalkonium Chloride | 0.01 |
| Sodium Chloride | 0.8 |

-continued

| Component | % w/v |
|---|---|
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

PEO-35-CO is sterilized by filtration. The sterilized anti-inflammatory product is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drag suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 4

Formulation for oral administration:

Tablet:
1–1000 mg of at least one PEO-CO with inactive ingredients such as starch, lactose and magnesium stearate can be formulated according to procedures known to those skilled in the art of tablet formulation.

EXAMPLE 5

Formulation for intraocular injection:

| Component | each mL contains: |
|---|---|
| PEO-CO | 0.1–1.0 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide | q.s., pH to approx. 7.2 |
| Water for injection | q.s. |

EXAMPLE 6

Preferred formulation for a topical ocular solution:

| Component | % w/v |
|---|---|
| PEO-35-CO | 5% |
| Benzalkonium chloride | 0.01% |
| HPMC | 0.5% |
| Sodium chloride | 0.8% |
| Sodium phosphate | 0.28% |
| Edetate disodium | 0.01% |
| NaOH/HCl | q.s. pH 7.2 |
| Purified Water | q.s. 100 mL |

EXAMPLE 7

Preferred bio-replacement formulations for intra-ocular administration:

| Ingredient | each mL contains: |
|---|---|
| PEO-35-CO | 0.01–0.1 (% w/v) |
| Sodium chondroitin sulfate | 40 mg |
| Sodium hyaluronate | 30 mg |
| Sodium dihydrogen phosphate hydrate | 0.45 mg |
| Disodium hydrogen phosphate | 2.00 mg |
| Sodium chloride | 4.3 mg |
| Purified water | q.s. |

The present invention is further illustrated by the following in vivo experiments:

EXAMPLE 8

The efficacy of PEO-COs to inhibit the inflammatory response of neutrophil influx, as compared to other agents, was tested in a rabbit trauma-induced inflammation model (van Delft, Comparison of the Effects of Corticosteroids and Indomethacin on the Response of the Blood-Aqueous Barrier to Injury, Current Eye Research, volume 6, No. 3, pages 419–425 (1987)). Briefly, New Zealand Albino (NZA) rabbits were dosed topically with the appropriate agent 45 minutes before induced-trauma. At that time, the eye was punctured with a small gauge needle and approximately 150 ml of aqueous humor was drawn out of the anterior chamber. Three hours after paracentesis, the animals were euthanitized, and the irisciliary body (ICB) was removed for leukocyte influx measurements.

The neutrophil (PMN) content was assessed indirectly by the determination of myeloperoxidase activity. Ocular PMN content in each treated group was then compared with that observed in the vehicle treated group using Dunnett's t-test. The results are illustrated in Table 1, below:

TABLE 1

Paracentesis-Induced Neutrophil Influx into Iris Ciliary Body at 3 Hours

| Treatment Group | ICB Myeloperoxidase (nmoles/min/mg ± SD) | % Inhibition |
|---|---|---|
| Maxidex Vehicle | 1,639 ± 593 | control |
| Dexamethasone 0.1% | 422 ± 326* | 74 |
| PEO-35-CO 5% | 608 ± 406* | 63 |
| Voltaren ® | 852 ± 601* | 48 |
| Diclofenac 0.1% in PEO-35-CO 5% | 773 ± 611* | 53 |

TABLE 1-continued

Paracentesis-Induced Neutrophil Influx into
Iris Ciliary Body at 3 Hours

| Treatment Group | ICB Myeloperoxidase (nmoles/min/mg ± SD) | % Inhibition |
|---|---|---|
| Diclofenac 0.1% in Maxidex Vehicle | 893 ± 569* | 46 |

*p < 0.01 Dunnett's t-test

The data of Table 1 illustrates the efficacy of PEO-35-CO in inhibiting PMN influx. PEO-35-CO was more effective than Diclofenac alone. Additionally, no additive effects were observed in the combination of PEO-35-CO and diclofenac.

EXAMPLE 9

The efficacy of PEO-COs to inhibit ocular inflammation in an endotoxin-induced rat uveitis model was assessed (Bhattacherjee, An Evaluation of Ocular Inflammation Following the Injection of Bacterial Endotoxin into the Rat Foot Pad, *Investigative Ophthalmology and Visual Science*, volume 24, pages 196–202 (1983)). Briefly, uveitis was induced by the subplantar injection of endotoxin (200 mg in 0.1 mL saline) in the right hind paw of female Lewis rats (5/group). PEO-35-CO (5% w/v) or carbopol vehicle (5/µL) was administered topically to each eye of the experimental animal at the time of endotoxin injection and again 4 hours later. Twenty-four (24) hours post endotoxin injection, animals were sacrificed by $CO_2$ inhalation, and total ocular neutrophil (PMN) content was assessed indirectly by determination of myeloperoxidase activity. Ocular PMN content in each treated group was then compared with that observed in the vehicle treated group using Dunnett's test. The results indicated a 67% inhibition of PMN influx over the control vehicle.

EXAMPLE 10

The efficacy of PEO-COs to inhibit monocyte cell adhesion to human vascular endothelial cells was investigated (Dicorieto, Characterization of the Adhesion of the Human Monocytic Cell Line U937 to Cultured Endothelial Cells, *Journal of Clinical Investigation*, volume 75, pages 1153–1161 (1985)). This was carried out by measuring the adhesion of U-937 (human histiocytic lymphoma) cells to Interleukin -1β (IL-1β)-stimulated human microvessel endothelial cells (HMVEC). The vascular endothelial cells were grown in 12-well plates and pretreated for 17 hours with varying concentrations of PEO-35-CO. IL-1β (10 ng/ml) was then added to the wells, and the endothelial cells were reincubated for an additional 4 hours. U-937 cells that had been labeled with $^{51}Cr$ were co-incubated with the HMVEC for 1 hour at 37° C. The wells were gently washed 3 times to remove unbound U-937 cells. Adherent U-937 cells (those bound to the vascular endothelial bed) were then solubilized in 1% SDS, and an aliquot of the lysate was counted on the gamma counter. Data is expressed as mean percent inhibition of 51Cr counts in triplicate test wells from two separate experiments compared to IL-1µ stimulated HMVEC (Table 2).

TABLE 2

IL-1B Stimulated U-937 Cell Adhesion

| Concentration % v/v* | % Inhibition of U-937 Adhesion |
|---|---|
| 0.01 | −4.66 ± 28.83 |
| 0.02 | 13.70 ± 19.42 |
| 0.03 | 22.30 ± 30.16 |
| 0.04 | 54.67 ± 19.79 |
| 0.05 | 72.45 ± 12.52 |

*% volume/volume

The cells remained viable at all PEO-35-CO concentrations tested, and the morphology of the cells was unaltered at concentrations from 0.01% to 0.05% v/v. The data of Table 2 indicates that PEO-35-CO dose-dependently inhibited U-937 cell adhesion to human microvascular endothelial cells ($IC_{50} \approx 0.035\%$ v/v).

What is claimed is:

1. A composition for treating inflammation comprising an effective amount of at least one PEO-CO in a pharmaceutically acceptable carrier,
    wherein the PEO-CO is the only active pharmaceutical agent in the carrier.

2. The composition of claim 1, consisting essentially of the PEO-CO in a pharmaceutically acceptable carrier.

3. The composition of claim 1, wherein the PEO-CO is PEO-35-CO.

4. The composition of claim 1, wherein the carrier further comprises a physiologically balanced irrigating solution.

5. The composition of claim 4, wherein the PEO-CO is PEO-35-CO.

6. The composition of claim 1, wherein the carrier comprises: sodium chloride, calcium chloride, magnesium chloride, sodium acetate, sodium titrate and water.

7. The composition of claim 1, wherein the carrier comprises:
    from about 0.000005 to about 0.1% w/v of an antioxidant/free radical scavenger;
    from about 1 to about 25 mM of dextrose;
    from about 0.01 to about 0.5% w/v of the PEO-CO for the treatment of inflammation;
    from about 50 to about 500 mM $Na^+$;
    from about 1 to about 10 mM $K^+$;
    from about 0.1 to about 5 mM $Ca^{++}$;
    from about 0.1 to about 10 mM $Mg^{++}$;
    from about 50 to about 500 mM $Cl^-$;
    from about 10 to about 50 mM bicarbonate; and
    from about 0.1 to about 5 mM phosphate.

8. The composition of claim 7, wherein the PEO-CO is PEO-35-CO.

9. The composition of claim 1, wherein the composition comprises a first part and a second part, the first part comprising a basic solution comprising a bicarbonate and a buffer, and the second part comprising an acidic solution containing an antioxidant/free radical scavenger, an energy source and divalent electrolytes, and wherein at least one PEO-CO and monovalent electrolytes are contained in either the first part or the second part.

10. The composition of claim 9, wherein the antioxidant/free radical scavenger is oxidized glutathione.

11. A composition for the treatment of inflammation comprising at least one PEO-CO in a bioreplacement fluid,
    wherein the PEO-CO is the only active pharmaceutical agent in the carrier.

12. The composition of claim 11, wherein the composition further comprises one or more glycosaminoglycans.

13. A method of treating inflammation in a human patient which comprises administering a pharmaceutical composition comprising an effective amount of at least one PEO-CO to the human patient, wherein the PEO-CO is the only active pharmaceutical agent in the composition.

14. A method of treating inflammation during surgery in a human patient which comprises administering a physiologically balanced irrigating solution comprising an effective amount of at least one PEO-CO to the human patient, wherein the PEO-CO is the only active pharmaceutical agent in the solution.

15. The method of claim 14, wherein the surgery is intra-vitreal or intra-cameral surgery.

16. The method of claim 14, wherein the PEO-CO is PEO-35-CO.

17. The method of claim 14, wherein the irrigating solution further comprises: sodium chloride, calcium chloride, magnesium chloride, sodium acetate, sodium citrate and water.

18. The method of claim 14, wherein the irrigating solution further comprises:

from about 0.000005 to about 0.1% w/v of an antioxidant/free radical scavenger;

from about 1 to about 25 mM of dextrose;

from about 0.01 to about 0.5% w/v of the PEO-CO for the treatment of inflammation;

from about 50 to about 500 mM $Na^+$;

from about 1 to about 10 mM $K^+$;

from about 0.1 to about 5 mM $Ca^{++}$;

from about 0.1 to about 10 mM $Mg^{++}$;

from about 50 to about 500 mM $Cl^-$;

from about 10 to about 50 mM bicarbonate; and from about 0.1 to about 5 mM phosphate.

19. The method of claim 18, wherein the PEO-CO is PEO-35-CO.

20. The method of claim 14, wherein the composition comprises a first part and a second part, the first part comprising a basic solution comprising a bicarbonate and a buffer, and the second part comprising an acidic solution containing an antioxidant/free radical scavenger, an energy source and divalent electrolytes, and wherein at least one PEO-CO and monovalent electrolytes are contained in either the first part or the second part.

21. The method of claim 20, wherein the antioxidant/free radical scavenger is glutathione.

22. A method of treating inflammation during surgery requiring the administration of a bioreplacement fluid in a human patient which comprises administering a composition comprising an effective amount of at least one PEO-CO in a bioreplacement fluid to the human patient, wherein the PEO-CO is the only active pharmaceutical agent in the composition.

23. The method of claim 22, wherein the PEO-CO is PEO-35-CO.

24. The method of claim 22, wherein the bioreplacement fluid further comprises one or more glycosaminoglycans.

* * * * *